(12) United States Patent
Seegert

(10) Patent No.: US 8,523,832 B2
(45) Date of Patent: Sep. 3, 2013

(54) REDUCED-PRESSURE, LINEAR WOUND CLOSING BOLSTERS AND SYSTEMS

(75) Inventor: Charles Alan Seegert, San Antonio, TX (US)

(73) Assignee: KCI Licensing, Inc., San Antonio, TX (US)

(*) Notice: Subject to any disclaimer, the term of this patent is extended or adjusted under 35 U.S.C. 154(b) by 0 days.

(21) Appl. No.: 13/456,201

(22) Filed: Apr. 25, 2012

(65) Prior Publication Data

US 2012/0245628 A1    Sep. 27, 2012

Related U.S. Application Data

(62) Division of application No. 12/475,388, filed on May 29, 2009, now Pat. No. 8,187,237.

(60) Provisional application No. 61/057,803, filed on May 30, 2008, provisional application No. 61/078,114, filed on Jul. 3, 2008.

(51) Int. Cl.
*A61M 1/00* (2006.01)

(52) U.S. Cl.
USPC .......................................... 604/313; 604/319

(58) Field of Classification Search
USPC ........................... 604/293, 313, 319; 606/201
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

(Continued)

*Primary Examiner* — Melanie Hand

(57) ABSTRACT

A reduced-pressure, linear-wound closing bolster has a pivotable frame that moves from an extended position to a compressed position under the influence of reduced pressure. The closing bolster may have a first closing member, a second closing member, and an interior space. A manifold member is disposed within the interior space and may be coupled to the pivotable frame. When a reduced pressure is applied, the pivotable frame is urged from the extended position to the compressed position. A first gripping member for transmitting a closing force from the first closing member to a first edge of a linear wound may be attached. Likewise, a second gripping member for transmitting a closing force from the second closing member to a second edge of the linear wound may be attached. Systems and methods are also presented.

19 Claims, 6 Drawing Sheets

(56) References Cited

U.S. PATENT DOCUMENTS

| | | |
|---|---|---|
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,091,804 A | 5/1978 | Hasty |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,224,945 A | 9/1980 | Cohen |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielson |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2001/0029956 A1 | 10/2001 | Argenta et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0209574 A1 | 9/2005 | Boehringer et al. |
| 2007/0135777 A1 | 6/2007 | Greene et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2007041642 A2 | 4/2007 |

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurqi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surq., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

International Search Report for PCT International Application PCT/US09/45754; May 29, 2009.

Written Opinion for PCT International Application PCT/US09/45754; May 29, 2009.

REDUCED-PRESSURE, LINEAR WOUND CLOSING BOLSTERS AND SYSTEMS

RELATED APPLICATIONS

The present application is a divisional of U.S. patent application Ser. No. 12/475,388, filed May 29, 2009 now U.S. Pat. No. 8,187,237 entitled "Reduced-Pressure, Linear Wound Closing Bolsters and Systems", which claims the benefit, under 35 USC §119(e), of the filing of U.S. Provisional Patent Application Ser. No. 61/057,803, entitled "Reduced-Pressure, Linear-Wound Treatment System," filed May 30, 2008; and U.S. Provisional Patent Application Ser. No. 61/078,114, entitled "Reduced-Pressure, Linear Wound Closing Bolster and System," filed Jul. 3, 2008. All of these provisional applications are incorporated herein by reference for all purposes.

BACKGROUND

The present invention relates generally to medical treatment systems, and more particularly, to reduced-pressure, linear wound closing bolsters and systems.

Physicians perform millions of surgical procedures each year around the world. Many of the procedures are performed as open surgery and an increasing number are performed using minimally invasive surgery, such as arthroscopic, laparoscopic, and endoscopic procedures. However performed, surgical procedures involve acute wounds, e.g., an incision, in the skin and related tissue. In many instances, the incision is closed at the conclusion of the procedure using a mechanical apparatus, such as staples or sutures, and the wound is merely covered with a dry, sterile bandage.

The use of staples or sutures to close an acute wound may have undesirable side effects. For example, staples and sutures can proximate the wound edges tightly where they are applied, but in between such mechanical closing devices are gaps or areas that are not as tightly closed. This may lead to areas of high stress proximate the closing device interspersed with areas of relatively low stress in between. This may, in turn, influence scarring, healing time, and strength of the wound.

BRIEF SUMMARY

Shortcomings with certain aspects of linear wound care are addressed by the present invention as shown and described in a variety of illustrative embodiments herein. "Linear wound" refers generally to a laceration or incision whether in a line or not. According to an illustrative embodiment, a reduced-pressure, linear-wound closing bolster for managing a linear wound includes a pivotable frame having a first closing member, a second closing member, and an interior space. The pivotable frame is operable to move between an extended position and a contracted position. The closing bolster further includes a manifold member disposed within the interior space, a first gripping member coupled to the first closing member, and a second gripping member coupled to the second closing member. The first gripping member is for transmitting a closing force from the first closing member to a first edge of the linear wound. The second gripping member is for transmitting a closing force from the second closing member to a second edge of the linear wound.

According to another illustrative embodiment, a reduced-pressure, linear-wound closing bolster includes a first closing member for placing on a first side of the linear wound, a second closing member for placing on a second side of the linear wound, and a first connecting member. The bolster also includes a first pivot connector coupling a portion of the first closing member and the connecting member, a second pivot connector coupling a portion of the second member and the connecting member, and a manifold member coupled to an interior surface of the first closing member and an interior surface of the second closing member. The manifold member contracts when placed under a reduced pressure. The bolster also includes an interface fluidly coupled to the manifold for delivering a reduced pressure thereto.

According to another illustrative embodiment, a reduced-pressure, linear wound treatment system includes a closing bolster for placing on the patient's skin over a linear wound and operable to move between an extended position and a compressed position. The closing bolster comprises a pivotable frame having an interior space and a manifold disposed within the interior space and coupled to the pivotable frame. The system includes a sealing subsystem for providing a fluid seal between the closing bolster and the patient, and a reduced-pressure subsystem for delivering a reduced pressure to the sealing subsystem. The sealing subsystem and reduced-pressure subsystem are operable to deliver a reduced pressure to the closing bolster, and the closing bolster is operable under reduced pressure to go to the compressed position and thereby develop an inward force.

According to one illustrative embodiment, a reduced-pressure, anisotropic closing bolster includes an anisotropic manifold member operable under reduced pressure to contract more in a lateral direction than in a longitudinal direction. The anisotropic manifold member includes a plurality of longitudinal manifold members of a flexible manifold material, a plurality of reinforcing members, and an anisotropic bolster body formed by coupling the plurality of longitudinal manifold members and the plurality of reinforcing members. The anisotropic bolster body is operable under reduced pressure to contract more perpendicularly to the plurality of reinforcing members than parallel to the plurality of reinforcing members.

According to another illustrative embodiment, a method of applying a closing force to a linear wound on a patient includes providing a reduced-pressure, linear-wound closing bolster. Wherein the reduced-pressure, linear-wound closing bolster includes a manifold member and a pivotable frame that has an interior space and a first closing member and a second closing member. The first closing member has a first longitudinal edge and a second longitudinal edge. The second closing member has first longitudinal edge and a second longitudinal edge. The method includes placing the second longitudinal edge of the first closing member proximate a first edge of the linear wound and placing the second longitudinal edge of the second closing member proximate a second edge of the linear wound. The method also includes forming a fluid seal between the pivotable frame and the patient's skin, coupling a reduced-pressure subsystem to an interface to the manifold member, and activating the reduced-pressure source.

According to another illustrative embodiment, a method of manufacturing a reduced-pressure, linear-wound closing bolster includes forming a pivotable frame having first closing member, a second closing member, and an interior space, the pivotable frame operable to move between an extended position and a contracted position. The method includes disposing a manifold member within the interior space and providing a first gripping member operable to transmit a closing force from the first closing member to a first edge of a linear wound. The method also includes providing a second gripping member operable to transmit a closing force from the second closing member to a second edge of the linear wound. The method may further include coupling the manifold member to the pivotable frame such that when a reduced pressure is applied, the pivotable frame is urged from the extended position to the contracted position.

According to one illustrative embodiment, a reduced-pressure, linear-wound closing bolster for managing a linear wound includes a first closing member, a second closing member, a pivot connector coupling the first closing member and second closing member, and an interior space formed at least in part by the first closing member and the second closing member. The pivot connector is operable to move between an extended position and a compressed position. The closing bolster further includes a manifold member disposed within the interior space and coupled to the first closing member and second closing member such that when reduced pressure is applied, the pivotable frame is urged from the extended position to the compressed position. The closing bolster also includes a first gripping member for transmitting a closing force from the first closing member to a first edge of a linear wound and a second gripping member for transmitting a closing force from the second closing member to a second edge of the linear wound.

The illustrative embodiments may provide a number of advantages. A couple of examples follow. Technical advantages of the illustrative embodiments are perceived to include that the wound might be able to withstand more force during the healing process. Additionally, the wound edges that otherwise would not be tightly and smoothly approximated are healed in a tight position with the edges approximated. The time for the wound to gain strength may be decreased. It may also reduce the scar formation at the wound. These are just some possible examples.

Other objects, features, and advantages of the illustrative embodiments will become apparent with reference to the drawings and detailed description that follow.

BRIEF DESCRIPTION OF THE DRAWINGS

A more complete understanding of the method and apparatus of the present invention may be obtained by reference to the following Detailed Description when taken in conjunction with the accompanying Drawings wherein.

DETAILED DESCRIPTION

In the following detailed description of the illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
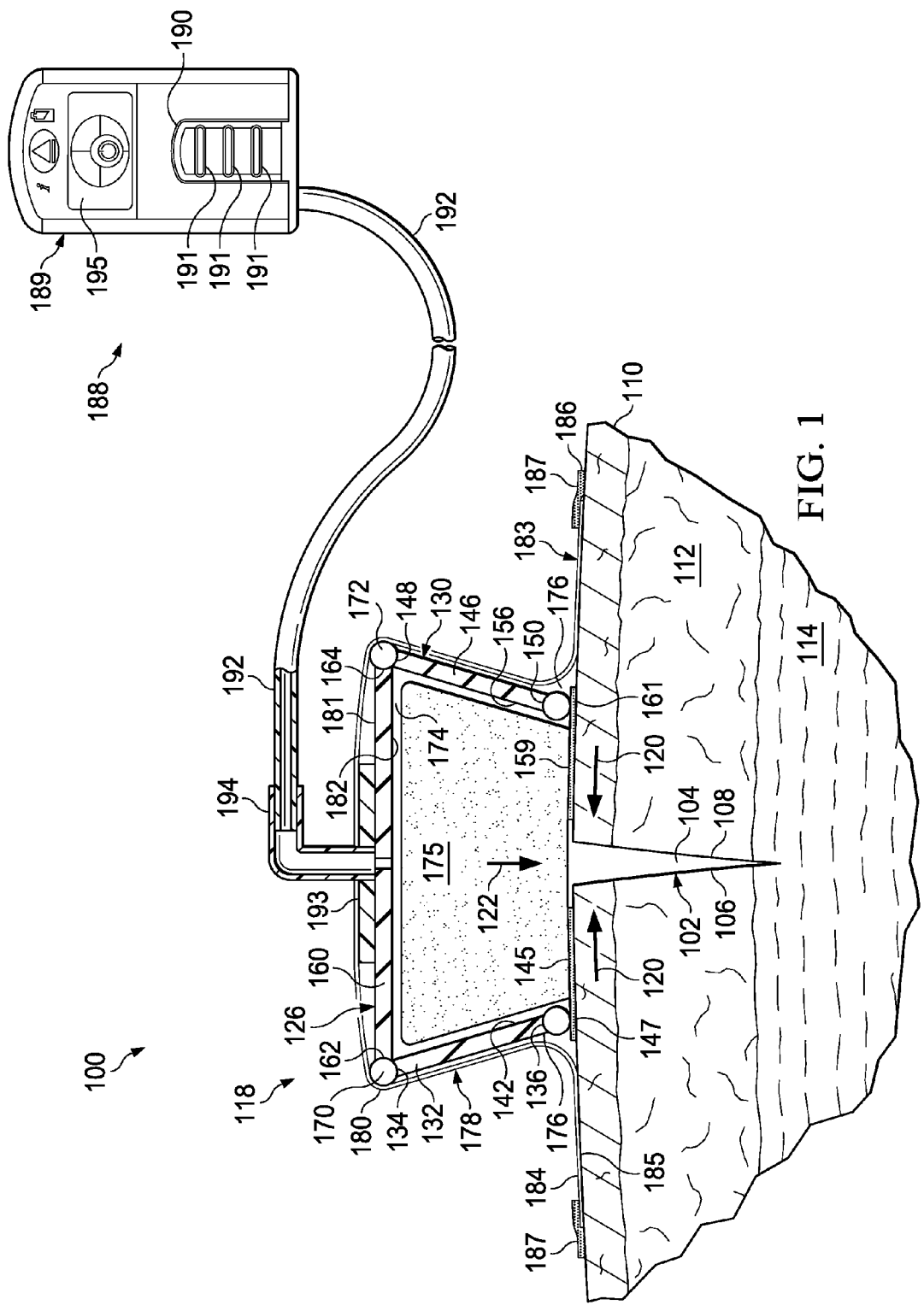
FIG. 1 is a schematic, cross-sectional view of an illustrative embodiment of a reduced-pressure, linear wound closing system.
Figure 2:
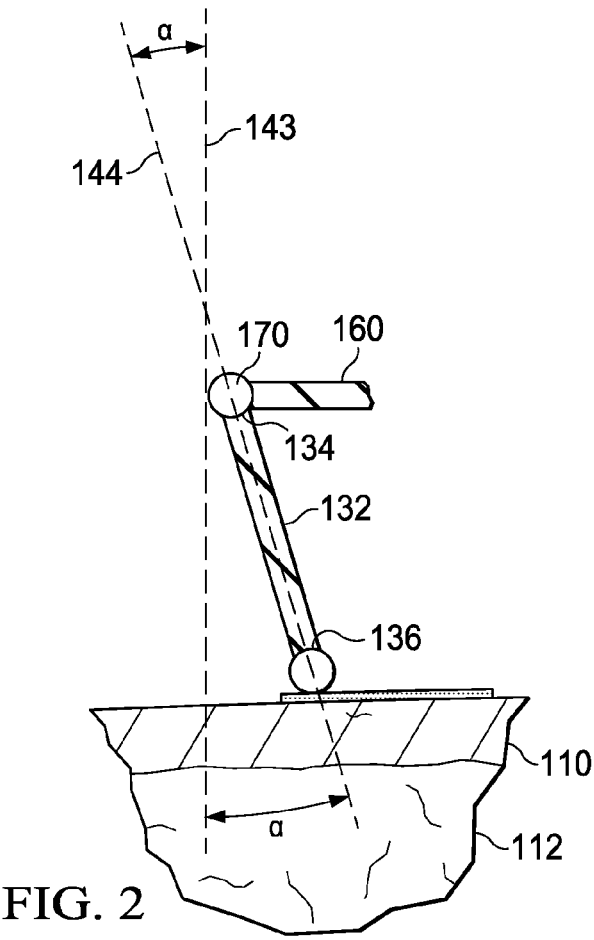
FIG. 2 is a schematic detail of a first closure member of the illustrative embodiment of FIG. 1.

Referring to FIGS. 1 and 2 an illustrative embodiment of a reduced-pressure linear wound closing system 100 for treating a linear wound 102, such as a laceration or, more typically, an incision 104 is presented. Linear wound 102 has a first edge 106 and a second edge 108. While linear wound 102 may extend to different depths, it is shown as an incision 104 extending through epidermis 110, dermis 112, and into subcutaneous tissue, or hypodermis, 114.

A dressing assembly 118 may be placed over the linear wound 102 and used with reduced pressure to supply an inward, or closing, force 120, and a compressive force 122 may be developed as well. Dressing assembly 118 includes a closing bolster 126 that is moveable between an extended position (e.g., FIG. 1) and a compression position. A sealing subsystem 178 provides a fluid seal between the dressing assembly 118 and the patient's epidermis 110. A reduced-pressure subsystem 188 provides reduced pressure to an interior portion of the dressing assembly 118 and causes the closing bolster 126 to be urged from the extended position to the compressed position and thereby provides the inward, closing force 124 to both edges 106, 108 of the linear wound 102.

Closing force 120 remains primarily within epidermis 110 and dermis 112. The closing force 120 may provide a smooth, tight approximation of edges 106 and 108 of the linear wound 102. In addition, system 100 is operable to deliver a reduced pressure to incision 104 that may also be realized at the level of any subcutaneous voids to help approximate—bring together—the tissues in that region as well as to help remove any air or any other fluids. The term "fluid" as used herein generally refers to gas or liquid, but may also include any other flowable material. A downward (for the orientation of FIG. 1) compression force 122 may also be developed.

The dressing assembly 118 may include closing bolster 126 and over-drape 180. The closing bolster 126 may be formed in many ways and has the effect of developing a closing force 120 when placed under reduced pressure. System 100 may further provide a compressive force 122, and at the same time, manifold reduced pressure to the linear wound 102 for reduced-pressure treatment.

In the illustrative embodiment of FIG. 1, closing bolster 126 is formed with a pivotable frame 130. To form the pivotable frame 130 of FIG. 1, a first closing member 132, second closing member 146, and a connection member 160 are coupled as will be described. The members of pivotable frame 130 may be made of any material, e.g., a medical grade silicone. The members of the pivotable frame 130 may be extruded, pour molded, injection molded, blow molded, or formed by other manufacturing techniques. The pivotable frame 130 is open on the ends (first end and second end, or proximal end and distal end) as the pivotable frame is deployed on the epidermis 110 and over the linear wound 102, but is covered by the over-drape 180 for use.

The first closing member 132 has a first longitudinal edge 134, second longitudinal edge 136, a first lateral edge (analogous to lateral edge 238 in FIG. 3B), second lateral edge (analogous to lateral edge 240 in FIG. 3B), an interior surface 142, and a lateral axis 144 (FIG. 2). Similarly, the second closing member 146 has a first longitudinal edge 148, second longitudinal edge 150, a first lateral edge (analogous to lateral edge 252 in FIG. 3B), second lateral edge (analogous to lateral edge 254 in FIG. 3B), an interior surface 156, and a lateral axis analogous to axis 144 (FIG. 2). The connection member 160 has a first longitudinal edge 162, a second longitudinal edge 164, a first lateral edge (analogous to first lateral edge 266 in FIG. 3B), and a second lateral edge (analogous to second lateral edge 268 in FIG. 3B).

The first longitudinal edge 134 of the first closing member 132 is pivotably coupled by a first pivot connector 170 to the first longitudinal edge 162 of the connection member 160. The first longitudinal edge 148 of the second closing member 146 is pivotably coupled by a second pivot connector 172 to the second longitudinal edge 164 of the connection member 160. Together, the pivotably coupled first closing member 132, second closing member 146, and connection member 160 form the pivotable frame 130 and further defines an interior space 174. In one variation, the pivotable frame 130 may be formed by using a first pivot connector to couple the first longitudinal edge 134 of the first closing member 132 to the first longitudinal edge 148 of the second closing member 146.

The first pivot connector 170 may be any device or system that holds the first longitudinal edge 134 of the first closing member 132 to the first longitudinal edge 162 of the connection member 160 (or first longitudinal edge 143 of the second closing member 146) and allows relative movement. The first pivot connector 170 may be, for example, a piano hinge, a living hinge, butterfly hinge, strap hinge, a filament-tape connection, tape, etc. The pivot connector 170 may also be a relief in a sheet of material that allows the sheet to fold and bend along an edge. The other connectors herein, e.g., connector 172, may also be any type of connector, such as those referenced in this paragraph.

A first gripping member 145 may be associated with the second longitudinal edge 136 of the first closing member 132, and a second gripping member 159 may be associated with the second longitudinal edge 150 of the second closing member 146. The gripping member 145, 159 may be a first adhesive strip 147 and a second adhesive strip 161, respectively. Alternatively, the edges 136, 150 may have high-friction members, e.g., soft silicone, added that are able to provide a friction interface with the skin such that as the edges 136, 150 are moved the skin moves with the edges 136, 150 without any significant slipping therebetween. The gripping member 145 and 159 are operable to transmit the inward, closing forces 120 from the closing members 132 and 146 to the patient's skin and thereby urge the edges 106 and 108 of the linear wound 102 into close approximation.

A manifold member 175 is disposed within the interior space 174 of the pivotable frame 130 and may be coupled to the interior surface 142 of first closing member 132 and to the interior surface 156 of second closing member 146. In an alternative embodiment, the manifold member 175 may not be coupled to the interior space 174 and reduced pressure may primarily move the first closing member 132 and second closing member 146 towards each other. The manifold member 175 contracts when placed under reduced pressure and is operable to distribute a reduced pressure to the linear wound 102. The manifold member 175 may be made from many possible manifold materials.

The term "manifold" as used herein as a noun generally refers to a substance or structure that is provided to assist in applying reduced pressure to, delivering fluids to, or removing fluids from a tissue site. In one illustrative embodiment, the manifold member 175 is made from a porous and permeable foam-like material and, more particularly, a reticulated, open-cell polyurethane or polyether foam that allows good permeability of wound fluids while under a reduced pressure. One such foam material that has been used is the VAC® Granufoam® Dressing available from Kinetic Concepts Inc. (KCI) of San Antonio, Tex. Any material or combination of materials might be used for the bolster material provided that the bolster material is operable to manifold the reduced pressure and contract under reduced pressure. A manifold typically includes a plurality of flow channels or pathways that are interconnected to improve distribution of fluids provided to and removed from the area of tissue around the manifold. Examples of manifolds may include without limitation devices that have structural elements arranged to form flow channels, cellular foam such as open-cell foam, porous tissue collections, and liquids, gels and foams that include or cure to include flow channels. The bolster material might also be a combination or layering of materials; for example, a first bolster layer of hydrophilic foam might be disposed adjacent to a second bolster layer of hydrophobic foam to form the bolster material.

The reticulated pores of the Granufoam® material, that are in the range of about 400 to 600 microns, are helpful in carrying out the manifold function, but other materials may be used. A material with a higher density (smaller pore size) than Granufoam® material may be desirable in some situations. The manifold member 175 may be a reticulated foam that is later felted to a thickness of about ⅓ the manifold member's 175 original thickness. Among the many possible materials, the following might be used: Granufoam® material or a Foamex technical foam (www.foamex.com). In some instances it may be desirable to add ionic silver to the foam in a microbonding process or to add other substances to the manifold member 175 such as antimicrobial agents. The manifold member 175 may be isotropic or anisotropic depending on the exact orientation of the forces 120, 122 that are desired during reduced pressure. The manifold member 175 could also be a bio-absorbable material.

Sealing subsystem 178 may include an over-drape 180, or drape, which has a first side 181 and a second side 182. The over-drape 180 covers the dressing 118 and extends past a peripheral edge 176 of bolster 126 to form a drape extension 183. Drape extension 183 has a first side 184 and a second side 185. A sealing apparatus 186 may be used to seal the drape extension 183 to the patient. Sealing apparatus 186 may take numerous forms, such as an adhesive sealing tape 187, or drape tape or strip; double-side drape tape; adhesive; paste; hydrocolloid; hydrogel; or other sealing device. If a tape 187 is used, the tape 187 may be formed of the same material as the over-drape 180 with a pre-applied, pressure-sensitive adhesive on the second side 185 of the extension 183. An adhesive might also be used to provide a substantially fluid seal between the over-drape 180 and the epidermis 110 of the patient. Before the over-drape 180 is applied to the patient, the adhesive may have removable strips covering the adhesive removed, or the drape 180 may be applied and the tape 187 placed to form a seal.

Over-drape 180 may be an elastomeric material that has pore sizes less than about 20 microns. "Elastomeric" means having the properties of an elastomer and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Over-drape materials may include a silicone, 3M Tegaderm® drape material, acrylic drape material such as one available from Avery, or an incise drape material.

The over-drape 180 may or may not be coupled to the bolster 126. If coupled, the coupling may occur in many ways. Over-drape 180 and bolster 126 may be coupled using adhesives such as an acrylic adhesive, silicone adhesive, hydrogel, hydrocolloid, etc. Over-drape 180 and bolster 126 may be bonded by heat bonding, ultrasonic bonding, and radio frequency bonding, etc. The coupling may occur in patterns or more completely. Structure might be added to the bond to make the over-drape 180 behave anisotropically in a desired direction, i.e. to make an anisotropic drape material. An anisotropic drape material helps the dressing assembly 118 to primarily move in a given direction, i.e. only about a certain axis or axes. This may be particularly useful in a closing application.

Reduced-pressure subsystem 188 includes a reduced-pressure source 189, which can take many different forms. Reduced-pressure source 189 provides a reduced pressure as a part of system 100. The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. It is often desirable for the reduced-pressure source 189 to develop a continuous reduced pressure below atmospheric pressure and also to be able to deliver a dynamic pressure, i.e., to vary the reduced pressure in a cycle or operate in a continuous or intermittent mode. The operable range of reduced pressure may vary widely as needed, but would typically include 200 mm Hg below atmospheric. In order to maximize patient mobility and ease, reduced-pressure source 189 may be a battery-powered, single-use reduced-pressure generator. Such a pressure source 189 facilitates application in the operating room and provides mobility and convenience for the patient during the rehabilitation phase.

In the illustrative embodiment of FIG. 1, the reduced-pressure source 189 is shown having a battery compartment 195 and a canister region 190 with windows 191 providing a visual indication of the level of fluid within canister 190. An interposed membrane filter, such as hydrophobic or oleophobic filter, might be interspersed between a conduit, or tubing, 192 and the reduced-pressure source 189.

The reduced pressure developed by reduced-pressure source 189 is delivered through the delivery tube or conduit 192 to an interface 193, which might be an elbow port 194. In one illustrative embodiment, port 194 is a TRAC® technology port available from KCI of San Antonio, Tex. Interface 193 allows the reduced pressure to be delivered to the sealing subsystem 178 and received by the manifold member 175.

In the embodiment of FIGS. 1 and 2, application of reduced pressure from the reduced-pressure subsystem 188 causes the manifold member 175 to contract inward, but because over-drape 180 surrounds the pivotal frame 130, there is also a downward (for the orientation shown) force placed on the pivotal frame 130. In this particular embodiment, it is desirable to orient the members of the pivotal frame 130 so that the downward force will be translated into a contribution to the closing force 120. As shown in FIG. 2, this may be accomplished by placing the closing members 132 and 146 with an inward orientation. For example, first closing member 132 is shown in cross-section having a lateral axis 144 that makes an angle α with a reference line or axis 143 that is normal to epidermis 110. Thus, the inward angle α means that as a force is applied downward on connection member 160, the force will urge first member 132 to pivot about first pivot connection 170 and want to collapse inward. This helps to urge the epidermis 110 in the direction of the linear wound 102.

In operation, reduced-pressure, linear wound closing system 100 may be applied to further assist mechanical closure devices such as sutures or staples already applied, or may be the only and primary closing source for linear wound 102. In either case, the system 100 is applied by placing the first closing member 132 on first wound edge 106 and the second closing member 146 on the second wound edge 108. Gripping member 145 on second longitudinal edge 136 is used to engage first edge 106 of the wound 102. In the particular embodiment shown, the first gripping member 145 is an adhesive strip 147. Thus, the healthcare provider would remove visible backing from the adhesive strip 147 and the adhesive strip 147 would be applied proximate first edge 106. In a similar manner, the second gripping member 159 in this embodiment is an adhesive strip 161, and a backing may be removed and the strip 161 applied proximate the second edge 108 of the linear wound 102. Adhesive strips 147 and 161 are applied near edges 106 and 108 in a manner that places the closing members 132 and 146 at an inward angle as described earlier in connection with FIG. 2. It should be noted that in this particular embodiment, the manifold member 175 has already been placed within interior space 174 formed by the pivotal frame 130, but in other applications the manifold member 175 could be inserted just prior to applying the gripping members 145 and 159 to the epidermis 110. If the overdrape 180 has not already been coupled to an exterior surface of the pivotable frame 130, the overdrape 180 is then placed over the frame 130 and caused to extend beyond the peripheral edges 170 to form the drape extensions 183. In this particular embodiment, adhesive tape 187 is then applied to make sure a fluid seal is formed between drape 180 and the patient's epidermis 110. Reduced-pressure interface 193 is applied and is coupled to delivery tube 192, which in turn is coupled to the reduced-pressure source 189.

Reduced-pressure source 189 may then be activated to deliver reduced pressure to the sealing subsystem 178 and in particular to the manifold member 175. Subject to reduced pressure, manifold member 175 contracts and is compressed down along with the pivotal frame 130. The combination of forces urges the second lateral edges 140 and 154 towards each other and towards wound 102, provides some compression force down, and manifolds reduced pressure to the wound 102.

Figure 3A:
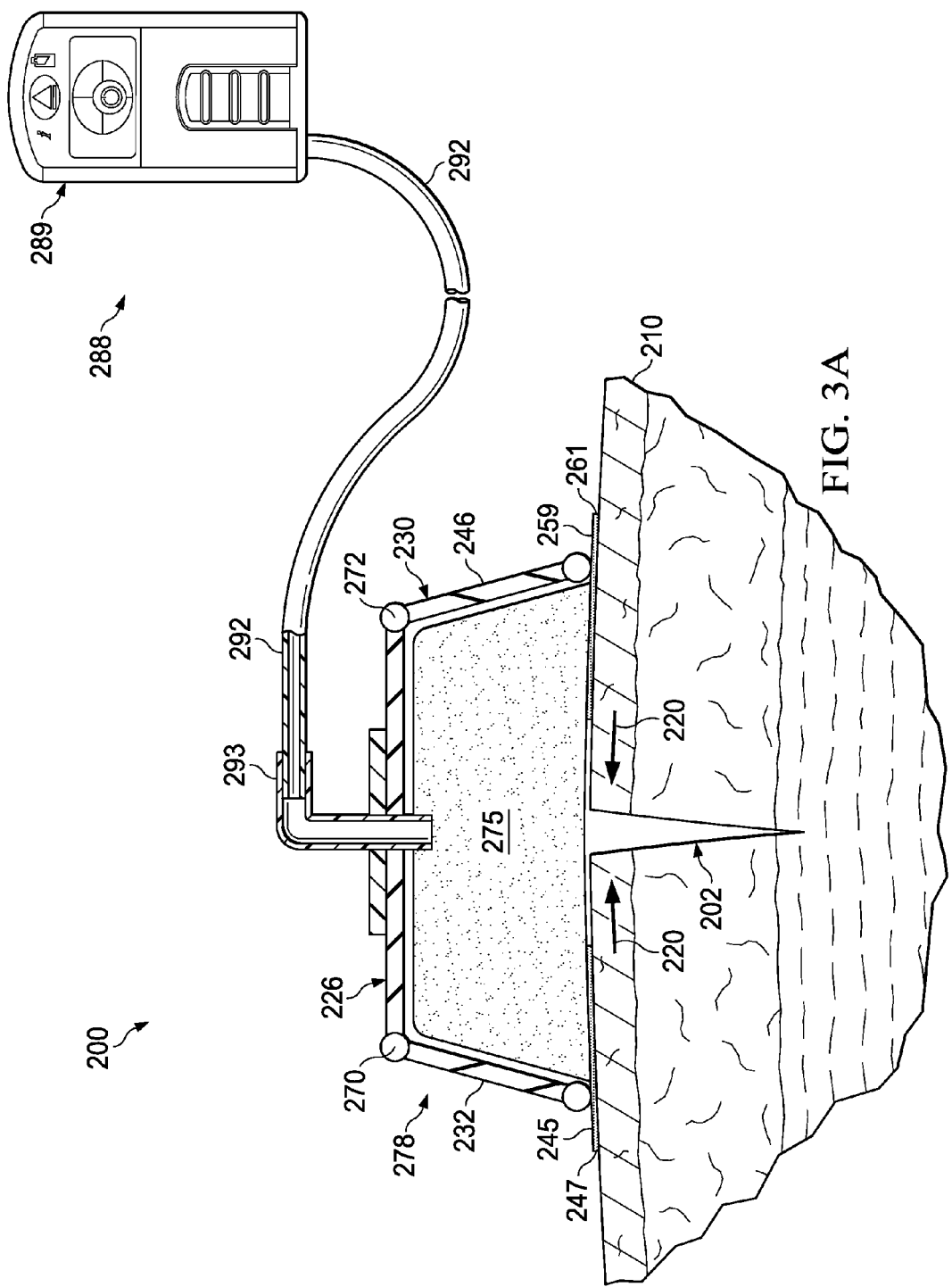
FIG. 3A is a schematic, cross-sectional view of an illustrative embodiment of a reduced-pressure, linear wound closing bolster shown in an extended position.
Figure 3B:
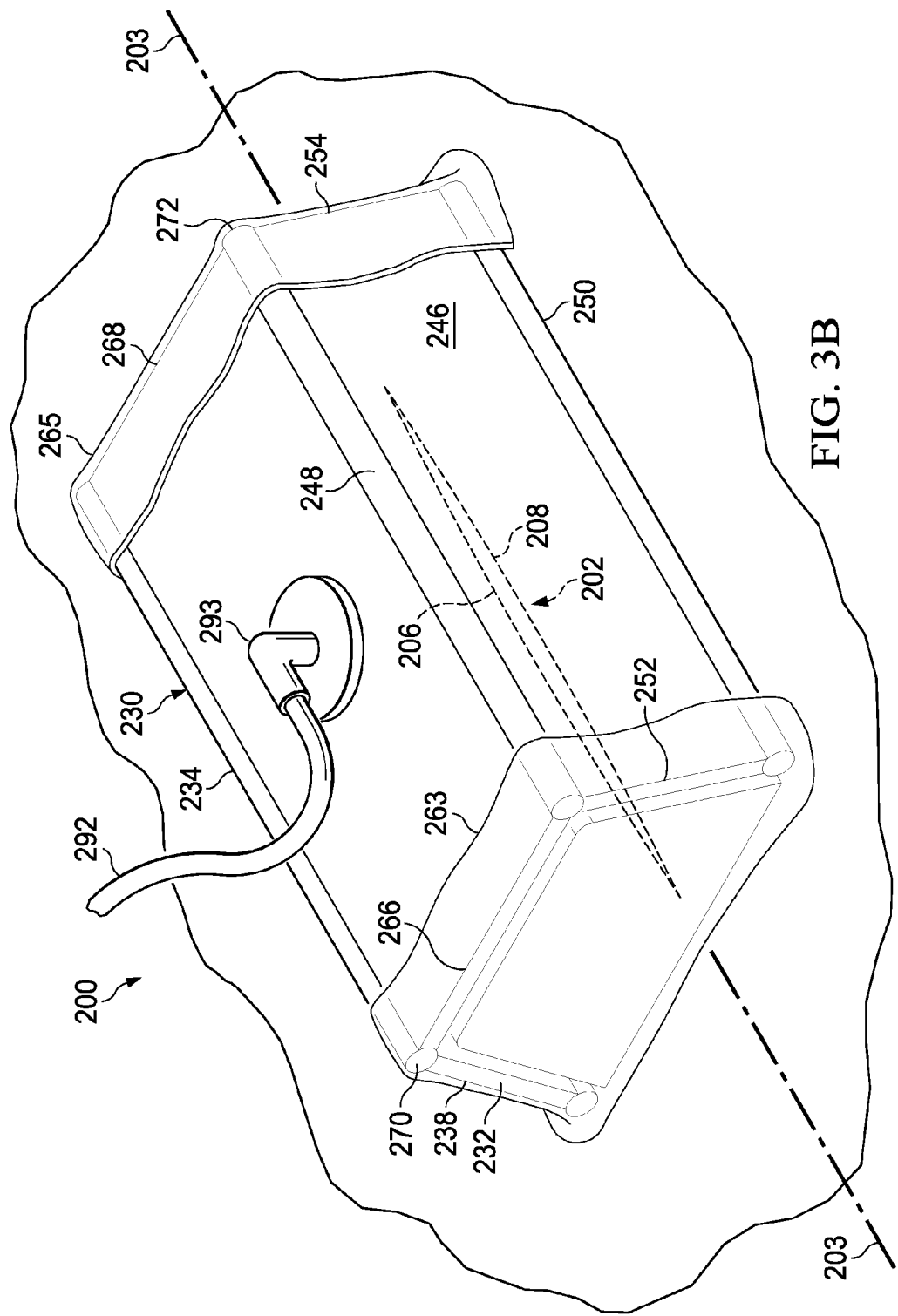
FIG. 3B is a schematic, perspective view of the closing bolster of FIG. 3A also shown in the extended position.
Figure 3C:
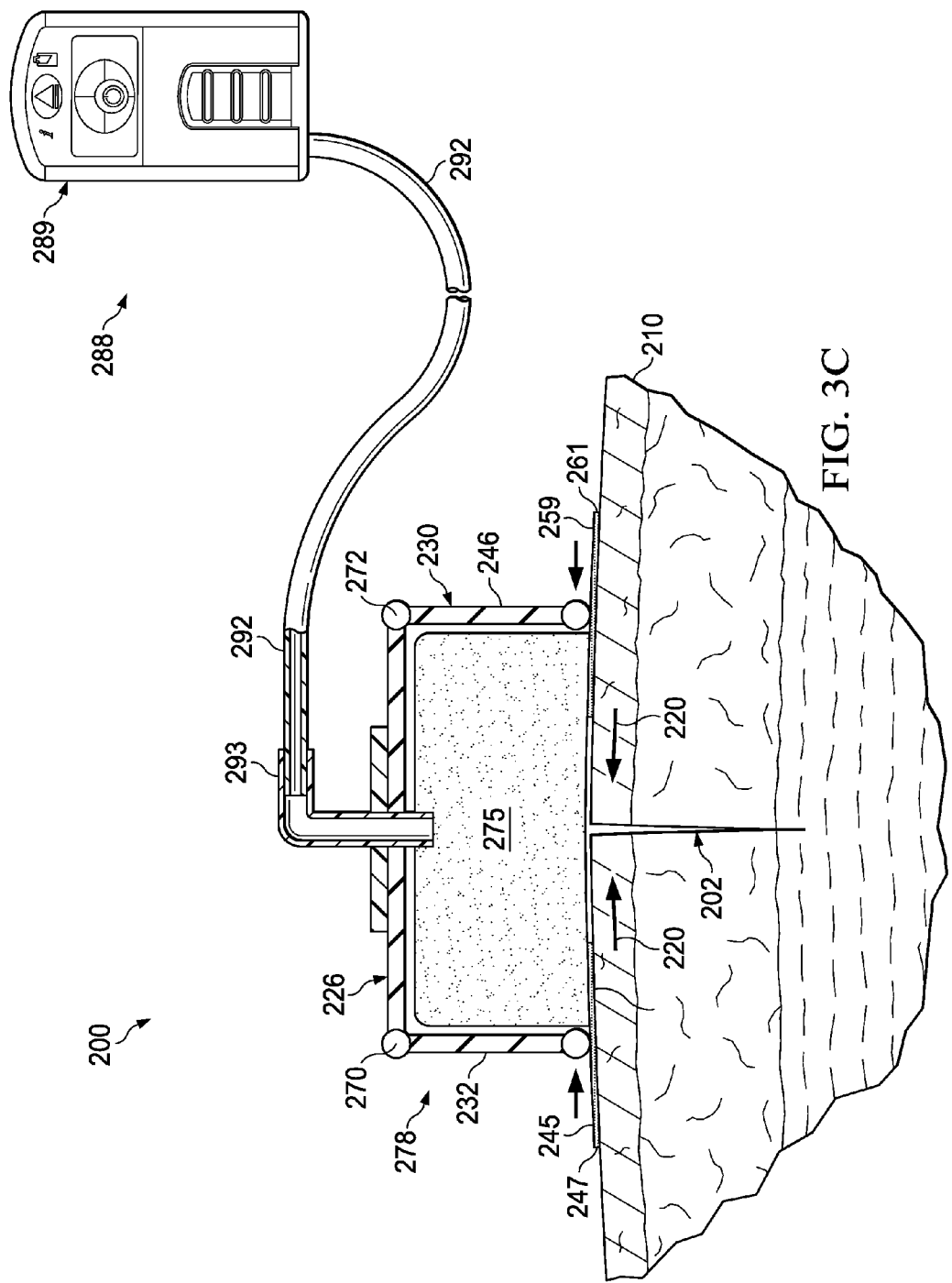
FIG. 3C is a schematic, cross-sectional view of the closing bolster of FIGS. 3A and 3B shown in a compression position.

Referring to FIGS. 3A, 3B, and 3C, another embodiment of a reduced-pressure, linear-wound closure system 200 is presented. Many of the parts are analogous to those of system 100 of FIGS. 1 and 2 and the possible relationship presented as such by simply indexing the numbers by 100. Referring particularly to FIG. 3A, two particular differences are noted. First, the sealing subsystem 278 does not involve the use of an overdrape, but provides a pivotable frame 230 to which a first end cap 263 (FIG. 3B) and a second end cap 265 (FIG. 3B) have been added to form a fluid seal. The interface 293 allows reduced pressure to be supplied to the manifold member 275 without compromising the fluid seal. Second, in application, the closing members 232 and 246 may be allowed to have an outward angle relative to reference line normal to the epidermis (analogous to reference line 143 of FIG. 2). This is because in this embodiment there will not generally be a downward compression force placed on the pivotable frame 230. The closing members 232 and 246 are urged together to provide the inward force 220 primarily by contraction of the manifold member 275. The application of reduced pressure to the manifold member 275 causes the closing bolster 226 to move from an extended position shown in FIGS. 3A and 3B to a compression position shown in FIG. 3C.

Referring to FIG. 3B, system 200 includes pivotal frame 130, which is shown positioned with a lengthwise dimension running parallel to wound axis 203 of linear wound 202. Linear wound 202 has first edge 206 and second edge 208. The first closing member 232 has first lateral edge 238 and a first longitudinal edge 234. The second closing member 246 has a first lateral edge 252 and a second lateral edge 254. The second closing member 246 also has first longitudinal edge 248 and second longitudinal edge 250.

End caps 263 and 265 may be formed in a number of different ways to provide a fluid seal to the ends of the pivotal frame 130. In this particular embodiment, they are shown as adhesive portions of an overdrape material that have been applied to cover the end pieces.

In systems 100 and 200, the reduced pressure delivered by reduced pressure subsystems 188 and 288 may be supplied in a continuous mode or a dynamic reduced pressure mode. In a dynamic mode, the pressure is varied in any number of different types of patterns. For example, referring to FIG. 4, one particular pattern for the application of reduced pressure is presented. The ordinate axis 310 gives the reduced pressure. It should be understood that an increase in reduced pressure here means that a lower gauge pressure would be shown. The abscissa axis 312 gives the elapsed time. Thus, in this particular pattern, the reduced pressure is ramped up to a baseline level 314 and then varied, in this instance, in a sinusoidal pattern between a greater reduced pressure level 316 and a lower reduced pressure 318. This variation in reduced pressure causes micromotion of the wound by varying the closing forces, e.g., the variation of the closing forces 120 and 220 of the embodiments of FIG. 1 and FIG. 3.

Figure 4:
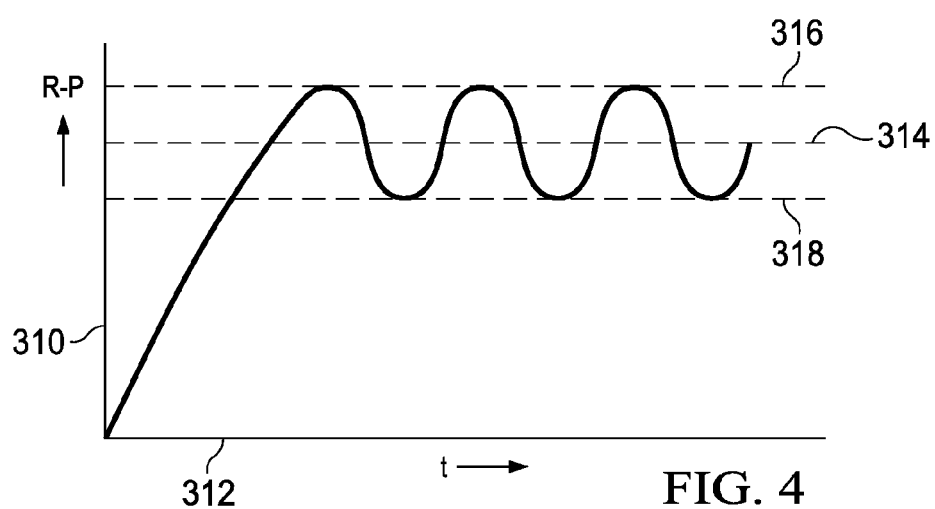
FIG. 4 is a schematic diagram showing one possible pattern for a dynamic reduced pressure delivered to a reduced-pressure, linear wound closure system.
Figure 5:
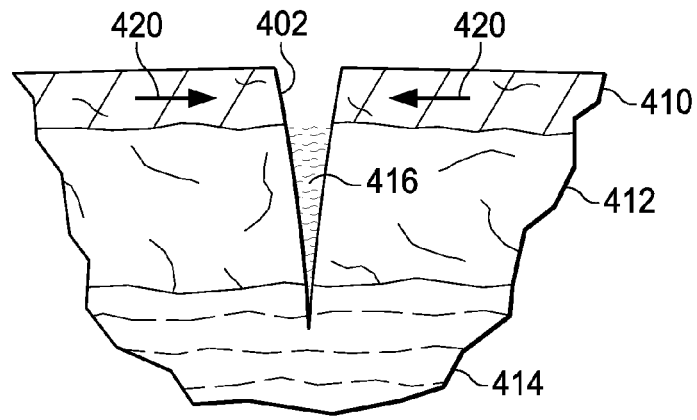
FIG. 5 is a schematic, cross-sectional view of a linear wound showing the development of collagen parallel to the closing force applied.

Referring now to FIG. 5, one of the beneficial effects encouraged by use of the dynamic pressure, such as the illustration given in connection with FIG. 4, is presented. A linear wound 402 through epidermis 410, dermis 412, and even into subcutaneous tissue 414 is shown. Linear wound 402 has been subjected to dynamic micromotion for forces 420 which may have been generated by a system such as system 100 or system 200, FIG. 1 and FIG. 3, respectively. The micromotion causes the collagen 416 to be deposited in the wound 402 with an orientation that is parallel to the forces 420.

Figure 6:
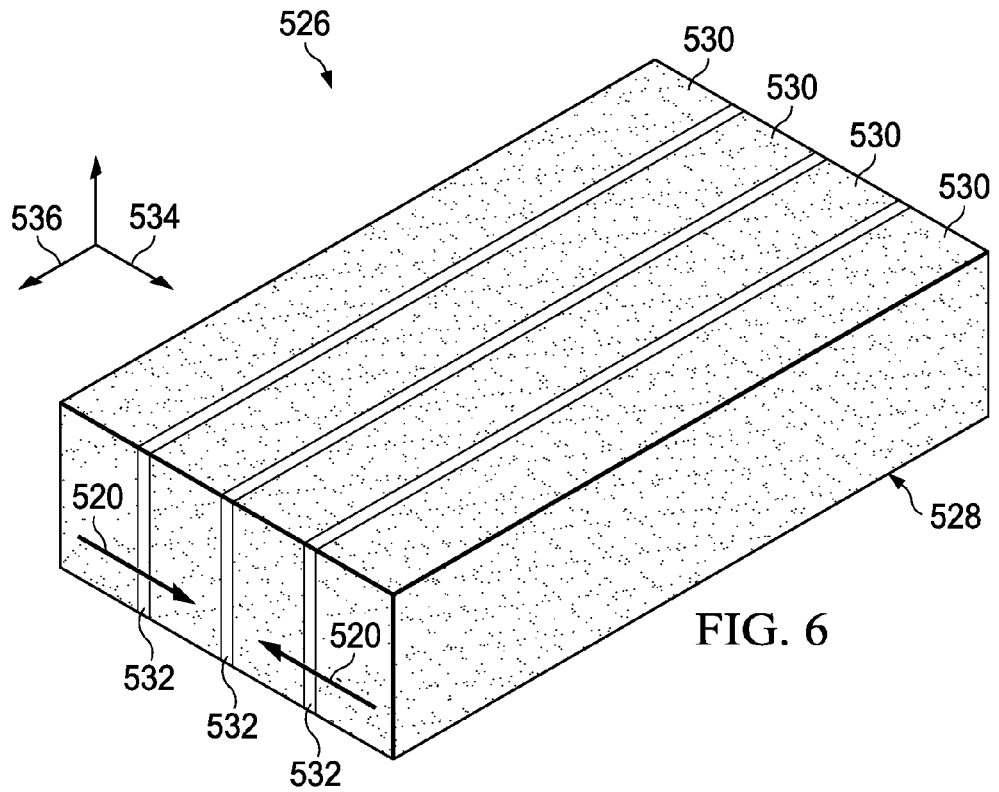
FIG. 6 is a schematic, perspective view of another illustrative embodiment of a closing bolster.

Referring now to FIG. 6, another embodiment of a system for providing a closing force to a linear wound is presented. In this system, an anisotropic bolster 526 is formed with an anisotropic body 528. The anisotropic body 528 comprises an anisotropic manifold member operable under reduced pressure to contract more in a lateral direction, i.e, parallel to force 520, than in a longitudinal, or lengthwise, direction, i.e., perpendicular to force 520.

The anisotropic body may be formed in many ways. As one illustrative embodiment, the bolster body 528 may be formed by utilizing a plurality of flexible, or compressible, manifold members 530 and a plurality of reinforcing longitudinal members 532. The plurality of flexible manifold members 530 may be analogous to the material from which manifold members 175 and 275 were made in previously described embodiments. The reinforcing longitudinal members 532 are formed of a material, or reinforcing material, that inhibits compression along one or more axes or directions. The reinforcing material may also inhibit expansion along one or more axes. The reinforcing material may inhibit both compression and expansion along one or more axes or directions. In one illustrative embodiment, the reinforcing longitudinal members 532 are filaments combined with the manifold members 530 to form the bolster body 528. It will be appreciated that for the orientation shown, the resulting anisotropic bolster body 528 will be able to contract or compress in a first direction 534, but not in a substantial way in a second direction 536.

In operation, the anisotropic closing bolster 526 will be placed down on a linear wound with the lengthwise dimension of the plurality of reinforcing members 532 running parallel to the wound, i.e., with the linear wound substantially parallel to direction 536. An overdrape analogous to drape 180 of system 100 may be applied over the bolster 526 and an interface, which is analogous to interface 193 of FIG. 1, may be applied in order to deliver reduced pressure. When reduced pressure is delivered to the anisotropic closing bolster 526, it will contract in the first direction 534 and this causes inward forces 520 to be directed on both edges of the wound, providing a closing force. The reduced pressure supplied to anisotropic bolster 526 may be dynamically varied as previously discussed or provided in a constant mode.

It should be apparent from the foregoing that an invention having significant advantages has been provided. While the invention is shown in only a few of its forms, it is not just limited but is susceptible to various changes and modifications without departing from the spirit thereof.

I claim:

1. A reduced-pressure, linear-wound closing bolster for managing a linear wound, the bolster comprising:
    a pivotable frame having a first closing member and a second closing member pivotably coupled together and forming an interior space between the first closing member and the second closing member;
    a manifold member disposed within the interior space;
    a first gripping member coupled to the first closing member; and
    a second gripping member coupled to the second closing member;
    wherein the pivotable frame is operable to move between an extended position and a contracted position under a reduced pressure applied to the manifold member to transmit a closing force to the linear wound through the first and second gripping members.

2. The reduced-pressure, linear-wound closing bolster of claim 1, wherein the pivotable frame further comprises:
    a connecting member;
    a first pivot connector coupling the first closing member and the connecting member; and
    a second pivot connector coupling the second closing member and the connecting member.

3. The reduced-pressure, linear-wound closing bolster of claim 1, wherein the pivotable frame further comprises:
    a pivot connector for coupling the first closing member and second closing member.

4. The reduced-pressure, linear-wound closing bolster of claim 1 wherein the first gripping member comprises a first adhesive strip and the second gripping member comprises a second adhesive strip.

5. The reduced-pressure, linear-wound closing bolster of claim 1 wherein the first gripping member comprises a first high-friction member coupled to the first closing member and the second gripping member comprises a second high-friction member coupled to the second closing member.

6. The reduced-pressure, linear-wound closing bolster of claim 1 wherein the pivotable frame is open on a first end and a second end.

7. A reduced-pressure, linear-wound closing bolster for closing a linear wound, the bolster comprising:
   a first closing member for placing on a first side of the linear wound, the first closing member having a first longitudinal edge, a second longitudinal edge, and an interior surface;
   a second closing member for placing on a second side of the linear wound, the second closing member having a first longitudinal edge, a second longitudinal edge, and an interior surface;
   a connecting member having a first longitudinal edge and a second longitudinal edge;
   a first pivot connector coupling the first longitudinal edge of the first closing member and the first longitudinal edge of the connecting member, wherein the first pivot connector allows movement of the first closing member with respect to the connecting member;
   a second pivot connector coupling the first longitudinal edge of the second closing member and the second longitudinal edge of the connecting member, wherein the second pivot connector allows movement of the second closing member with respect to the connecting member;
   a manifold member coupled to the interior surface of the first closing member and the interior surface of the second closing member, and wherein the manifold member contracts when placed under a reduced pressure; and
   an interface fluidly coupled to the manifold for delivering the reduced pressure thereto.

8. The closing bolster of claim 7 wherein the first closing member and second closing member each have a lateral axis in cross section and wherein the lateral axis of the first closing member and second closing member each form an angle α with respect to a reference line (in cross section) that is normal to a patient's skin, and wherein, α is a non-zero value such that when a force is placed on the bolster in the direction of the linear wound, the bolster will develop an inward force.

9. The closing bolster of claim 7, wherein
   wherein the first closing member further comprises a first lateral edge and a second lateral edge;
   wherein the second closing member further comprises a first lateral edge and a second lateral edge;
   wherein the connecting member further comprises a first lateral edge and a second lateral edge;
   further comprising:
   a first end cap associated with the first lateral edge of the first closing member, first lateral edge of the second closing member, and first lateral edge of the connecting member, and
   a second end cap associated with the second lateral edge of the first closing member, second lateral edge of the second closing member, and second lateral edge of the connecting member; and
   wherein the connecting member, first closing member, second closing member, first end cap, and second end cap are operable to form a fluid seal against a patient's skin.

10. A reduced-pressure, linear-wound closing bolster for managing a linear wound, the bolster comprising:
    a first closing member;
    a second closing member;
    a connecting member;
    a first pivot connector coupling the first closing member to the connecting member and a second pivot connector coupling the second closing member to the connecting member;
    and an interior space formed at least in part by the first closing member and the second closing member;
    a manifold member disposed within the interior space and coupled to the first closing member and second closing member;
    a first gripping member; and
    a second gripping member;
    wherein the first gripping member and the second gripping member are operable to apply a closing force to the linear wound under a reduced pressure applied to the manifold member.

11. The reduced-pressure, linear-wound closing bolster of claim 10, wherein:
    the first pivot connector is pivotably coupled to a longitudinal edge of the first closing member and to a first longitudinal edge of the connecting member; and
    the second pivot connector is pivotably coupled to a longitudinal edge of the second closing member and to a second longitudinal edge of the connecting member.

12. The reduced-pressure, linear-wound closing bolster of claim 10, wherein:
    the first pivot connector is a first hinge coupled to a longitudinal edge of the first closing member and to a first longitudinal edge of the connecting member; and
    the second pivot connector is a second hinge coupled to a longitudinal edge of the second closing member and to a second longitudinal edge of the connecting member.

13. The reduced-pressure, linear-wound closing bolster of claim 10, wherein:
    the first closing member, the second closing member, and the connecting member form a pivotable frame;
    the first pivot connector is a first bendable relief in the pivotable frame; and
    the second pivot connector is a second bendable relief in the pivotable frame.

14. The reduced-pressure, linear-wound closing bolster of claim 10, further comprising an interface fluidly coupled to the manifold member for delivering the reduced pressure thereto.

15. The reduced-pressure, linear-wound closing bolster of claim 3, wherein the pivot connector is a hinge coupled to a longitudinal edge of the first closing member and to a longitudinal edge of the second closing member.

16. The reduced-pressure, linear-wound closing bolster of claim 1, wherein the pivotable frame further comprises:
    a connecting member pivotably coupled along a first longitudinal edge to the first closing member and along a second longitudinal edge to the second closing member.

17. The reduced-pressure, linear-wound closing bolster of claim 1, wherein the pivotable frame further comprises:
    a connecting member pivotably coupled along a first longitudinal edge to the first closing member through a first hinge and along a second longitudinal edge to the second closing member through a second hinge.

18. The reduced-pressure, linear-wound closing bolster of claim 3, wherein the pivot connector is a bendable relief coupled to a longitudinal edge of the first closing member and to a longitudinal edge of the second closing member.

19. The reduced-pressure, linear-wound closing bolster of claim 1, further comprising an interface fluidly coupled to the manifold member for delivering the reduced pressure thereto.

\* \* \* \* \*